United States Patent
Takagi et al.

(10) Patent No.: US 8,175,370 B2
(45) Date of Patent: May 8, 2012

(54) AUTOMATIC CELL ANALYZER AND AUTOMATIC CELL ANALYZING METHOD

(75) Inventors: Kosuke Takagi, Tokyo (JP); Yuichiro Matsuo, Tokyo (JP); Yoshihiro Shimada, Tokyo (JP)

(73) Assignee: Olympus Corporation, Tokyo (JP)

( * ) Notice: Subject to any disclaimer, the term of this patent is extended or adjusted under 35 U.S.C. 154(b) by 592 days.

(21) Appl. No.: 12/377,324

(22) PCT Filed: Aug. 10, 2007

(86) PCT No.: PCT/JP2007/065722
§ 371 (c)(1),
(2), (4) Date: Feb. 12, 2009

(87) PCT Pub. No.: WO2008/020572
PCT Pub. Date: Feb. 21, 2008

(65) Prior Publication Data
US 2010/0202679 A1 Aug. 12, 2010

(30) Foreign Application Priority Data
Aug. 14, 2006 (JP) ................................. 2006-221109

(51) Int. Cl.
*G06K 9/60* (2006.01)
(52) U.S. Cl. .................. 382/133; 382/195; 430/333
(58) Field of Classification Search .................. 382/128, 382/133, 190, 195; 430/333, 335
See application file for complete search history.

(56) References Cited

U.S. PATENT DOCUMENTS

| | | |
|---|---|---|
| 5,989,835 A | 11/1999 | Dunlay et al. |
| 6,573,039 B1 | 6/2003 | Dunlay et al. |
| 6,620,591 B1 | 9/2003 | Dunlay et al. |
| 6,671,624 B1 | 12/2003 | Dunlay et al. |
| 6,727,071 B1 | 4/2004 | Dunlay et al. |
| 6,902,883 B2 | 6/2005 | Dunlay et al. |
| 7,060,445 B1 | 6/2006 | Dunlay et al. |
| 7,117,098 B1 | 10/2006 | Dunlay et al. |
| 7,235,373 B2 | 6/2007 | Dunlay et al. |
| 2006/0018013 A1* | 1/2006 | Suzuki et al. ................. 359/368 |

FOREIGN PATENT DOCUMENTS
JP 10-243289 A 9/1998
JP 2002-355090 A 12/2002

OTHER PUBLICATIONS

English Language International Search Report dated Nov. 6, 2007 issued in parent Appln. No. PCT/JP2007/065722.

* cited by examiner

*Primary Examiner* — Wensing Kuo
(74) *Attorney, Agent, or Firm* — Holtz, Holtz, Goodman & Chick, PC

(57) ABSTRACT

A sharp image showing a thin projecting part is acquired without using a complex dyeing method, and the analysis accuracy is improved. An automatic cell analyzer (1) comprises: an imaging unit (4) for capturing fluorescence emitted from a cell (S) and acquiring a cell image; an exposure changing section (5) for changing the exposure condition when the imaging unit (4) captures cell images; and a processing section (5) for analyzing the cell (S) on the basis of a plurality of cell images respectively captured under the changed exposure conditions.

7 Claims, 7 Drawing Sheets

AUTOMATIC CELL ANALYZER AND AUTOMATIC CELL ANALYZING METHOD

This application is a U.S. National Phase Application under 35 USC 371 of International Application PCT/JP2007/065722 filed Aug. 10, 2007.

TECHNICAL FIELD

The present invention relates to an automatic cell analyzer and an automatic cell analyzing method for automatically acquiring sample images of, for example, a cell, and for analyzing these images.

BACKGROUND ART

Conventionally, for example, a system for automatically analyzing cells so as to numerically quantify drug-induced damages on cells has been proposed (for example, refer to Patent Document 1).

This automatic cell analyzing system carries out image processing of captured images of cells to specify locations of, and/or boundaries between, cells in the images, and then carries out analysis through calculations of feature quantities, such as the size, length, etc. of these cells.

Patent Document 1:

Japanese Unexamined Patent Application, Publication No. 2002-355090

DISCLOSURE OF INVENTION

However, upon the microscopic observation of cells which have been treated with fluorescent dyeing or the like, the degree of the dyeing varies depending on each cell or each organ of cells, and the fluorescence intensity thereof is not fixed. For this reason, for example, upon the analysis of images of nerve cells, thin projecting parts extending from nerve cells like their legs are apt to be dyed insufficiently, which results in inaccuracy of the image analysis. Specifically, the disadvantage is such that the acquired image may show, due to the insufficient fluorescence intensity, as if a thin projecting part were segmented, although it is actually one continuously extending portion.

In this case, with respect to the thin projecting part, it can also be considered to concurrently use a dyeing method which specifically dyes the thin projecting part. However, such a concurrent use of a plurality of different dyeing methods involves complexity in the pretreatment process prior to the observation and in the treatment procedure performed by the experimenter. Such an arrangement needs a very long time for treating a large amount of samples. Therefore, it is required to reduce complex pretreatments as much as possible.

This invention takes the above situation into consideration with an object of providing an automatic cell analyzer and an automatic cell analyzing method, with which a sharp image showing a thin projecting part can be acquired without using a complex dyeing method, and the analysis accuracy can be improved.

In order to achieve the above object, the present invention provides the following solutions.

The present invention provides an automatic cell analyzer comprising: an imaging unit for capturing fluorescence emitted from a cell and acquiring a cell image; an exposure changing section for changing the exposure condition when the imaging unit captures cell images; and a processing section for analyzing the cell on the basis of a plurality of cell images respectively captured under the changed exposure conditions.

According to the present invention, the exposure condition is changed by the operation of the exposure changing section when the imaging unit captures cell images, so that thereby a plurality of cell images are captured under different exposure conditions. Then, the cell is analyzed by the operation of the processing section on the basis of the plurality of cell images respectively captured under the different exposure conditions.

Regarding minute parts of the cell such as a thin projecting part, since their fluorescence luminance is low, it becomes possible to avoid capturing the cell image which partially lacks the whole figure of the cell by setting the exposure condition such as extending the exposure time for the image pickup. On the other hand, regarding other parts having high fluorescence luminance such as the cell body, it becomes possible to avoid making the cell image too bright by setting the exposure condition such as shortening the exposure time for the image pickup.

In the above invention, the cell may be a nerve cell having a thin projecting part.

In this manner, a cell image showing a continuous figure of the nerve cell without segmentation of the thin projecting part can be acquired.

In addition, in the above invention, the exposure changing section may change between: a first exposure condition capable of capturing a first cell image with which the shape of the thin projecting part can be analyzed; and second exposure condition capable of capturing a second cell image with which the shape of another part than the thin projecting part can be analyzed.

By so doing, the shape of the thin projecting part and the shape of another than the projecting part of the cell can be both clearly analyzed on the basis of the first cell image captured under the first exposure condition and the second cell image captured under the second exposure condition.

Moreover, in the above invention, the processing section may detect the thin projecting part, on a basis of the diameter of an inscribed circle inscribing the profile shape of the cell image.

By so doing, a region in which inscribed circles of relatively small and comparable diameters are continuously arranged, can be readily detected as a thin projecting part.

The present invention also provides an automatic cell analyzing method comprising: a step of capturing fluorescence emitted from a cell under a first exposure condition, and acquiring a first cell image; a step of capturing fluorescence emitted from the cell under a second exposure condition that is different from the first exposure condition, and acquiring a second cell image; and a step of analyzing the cell on the basis of the first cell image and the second cell image.

In the above invention, the first exposure condition may be a condition under which correct exposure can be achieved for the cell body, and the second exposure condition may be a condition under which correct exposure can be achieved for a thin projecting part extending from the cell body.

The present invention demonstrates an effect of enabling the acquisition of a sharp image showing a thin projecting part without using a complex dyeing method, and improvement of the analysis accuracy.

EXPLANATION OF REFERENCE SIGNS

B: Thin projecting part
C: Inscribed circle
S: Cell sample (Cell)
1: Automatic cell analyzer
4: Imaging unit
5: Control unit (Exposure changing section, Processing section)

BEST MODE FOR CARRYING OUT THE INVENTION

Hereunder is a description of an automatic cell analyzer 1 and an automatic cell analyzing method according to one embodiment of the present invention, with reference to FIG. 1 to FIG. 7.

Figure 1:
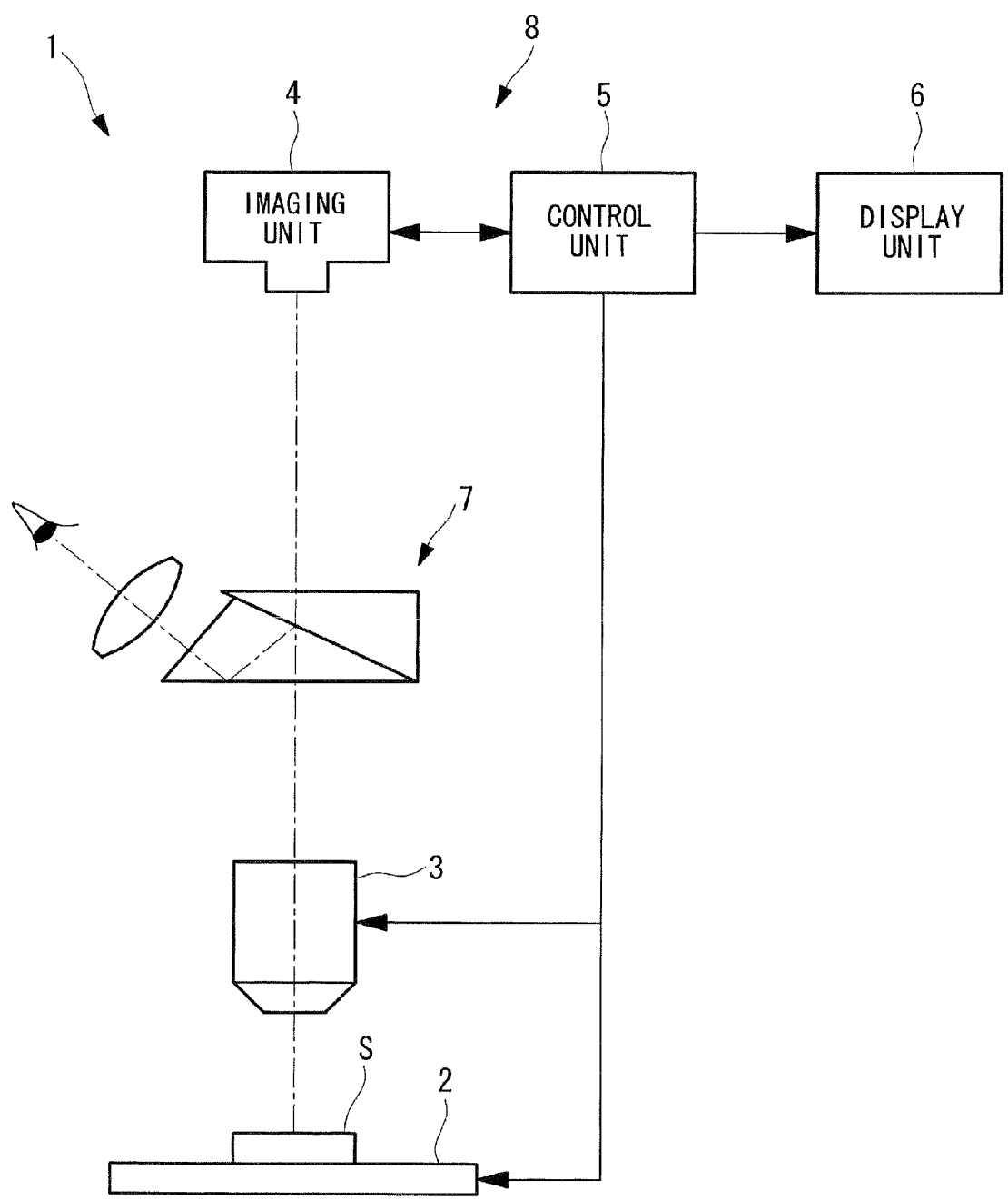
FIG. 1 is an overall block diagram schematically showing an automatic cell analyzer according to one embodiment of the present invention.

As shown in FIG. 1, the automatic cell analyzer 1 according to the present embodiment comprises: a stage 2 for mounting a cell sample S etc to move in two horizontal axial directions; an object lens 3 for converging fluorescence from the cell sample S; an imaging unit 4 such as a CCD camera for capturing an image using the fluorescence converged by the object lens 3; a control unit 5 for controlling these devices as well as processing the image captured by the imaging unit 4; and a display unit 6 for displaying the cell image processed by the control unit 5. In the drawing, the reference sign 7 denotes an eyepiece optical system for visually observing the cell sample S, either directly or through converged fluorescence from the cell sample S, with the object lens 3.

The cell sample S etc. is mounted on a slide glass or a multiplate.

The imaging unit 4 is to capture cell images under two different exposure conditions.

Figure 2A:
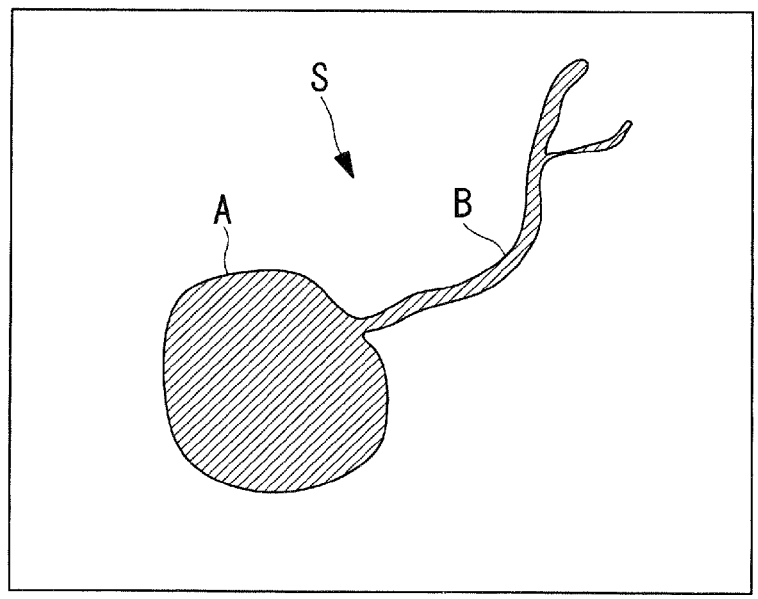
FIG. 2A shows an example of the actual figure of a cell sample analyzed by the automatic cell analyzer of FIG. 1.
Figure 2B:
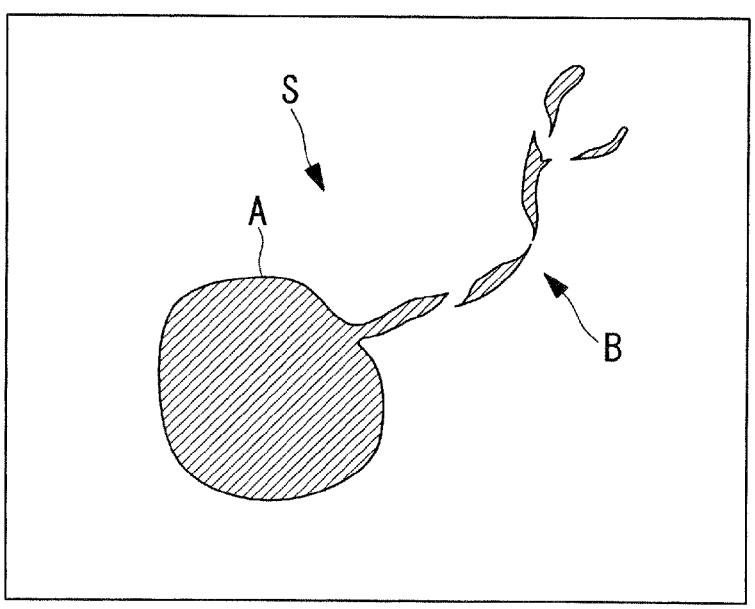
FIG. 2B shows an example of an image captured under a first exposure condition having a short exposure time, to be analyzed by the automatic cell analyzer of FIG. 1.

The first exposure condition is a condition for capturing an image of the cell sample S over a relatively short exposure time. This first exposure condition is an exposure condition under which: regarding the cell sample S whose actual figure is as shown in FIG. 2A; correct exposure can be achieved for the cell body A having a large area and a relatively high luminance as shown in FIG. 2B. In this case, the acquired image can achieve a sharp profile with regard to the cell body A, whereas only a fragmental image is achieved with regard to the thin projecting part B having a long-and-slender shape and a relatively low luminance due to insufficient exposure, and the acquired image shows an intermittent, that is to say, discontinuous and segmented, form.

Figure 3A:
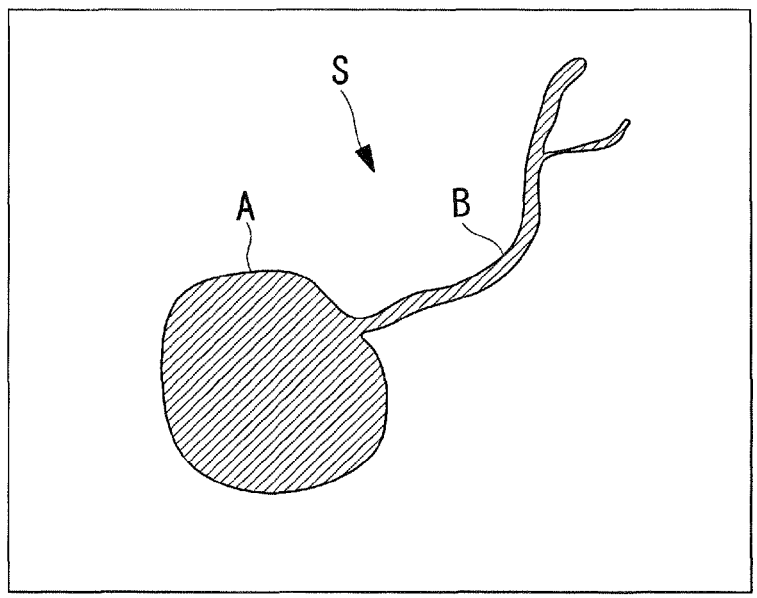
FIG. 3A shows an example of the actual figure of a cell sample analyzed by the automatic cell analyzer of FIG. 1.
Figure 3B:
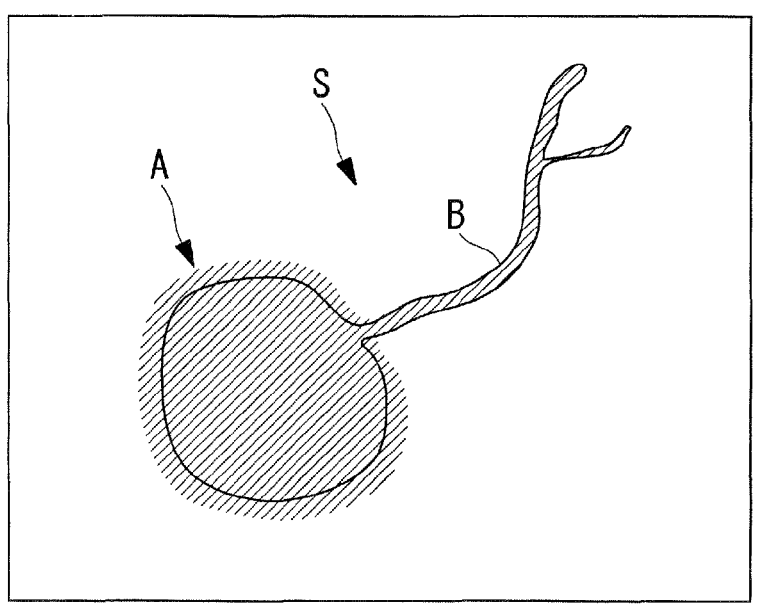
FIG. 3B shows an example of an image captured under a second exposure condition having a long exposure time, to be analyzed by the automatic cell analyzer of FIG. 1.

The second exposure condition is a condition for capturing an image of the cell sample S over an exposure time longer than that of the first exposure condition. Under this second exposure condition, conversely to the first exposure condition: regarding the cell sample S whose actual figure is as shown in FIG. 3A; correct exposure can be achieved for the thin projecting part B having a relatively low luminance as shown in FIG. 3B and the acquired image shows a continuous form thereof, whereas the acquired image shows a blurred profile image as for the cell body A having a relatively high luminance due to overexposure.

The control unit 5 carries out image processing on these two acquired images to compose a cell image which precisely expresses both the cell body A and the thin projecting part B of the cell sample S, so that the composed image can be displayed by the display unit 6.

Figure 4:
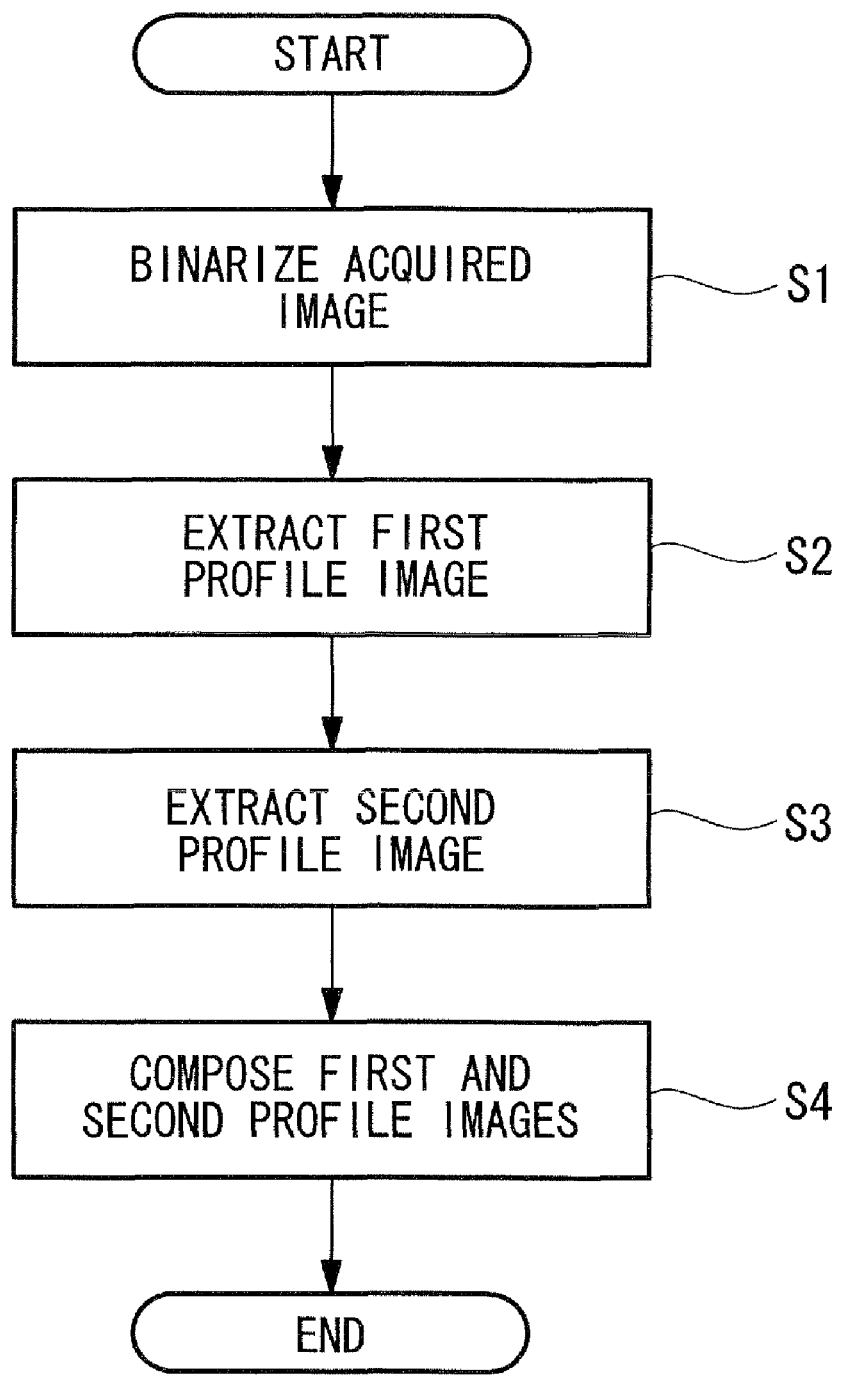
FIG. 4 is a flowchart showing an automatic cell analyzing method using the automatic cell analyzer of FIG. 1.

As shown in FIG. 4, in the image processing by the control unit 5, firstly, the acquired image is binarized to extract the profile (Step S1). The profile can be extracted by, for example, extracting pixels which are adjacent to pixels having different luminance in the binarized cell image.

Figure 5A:
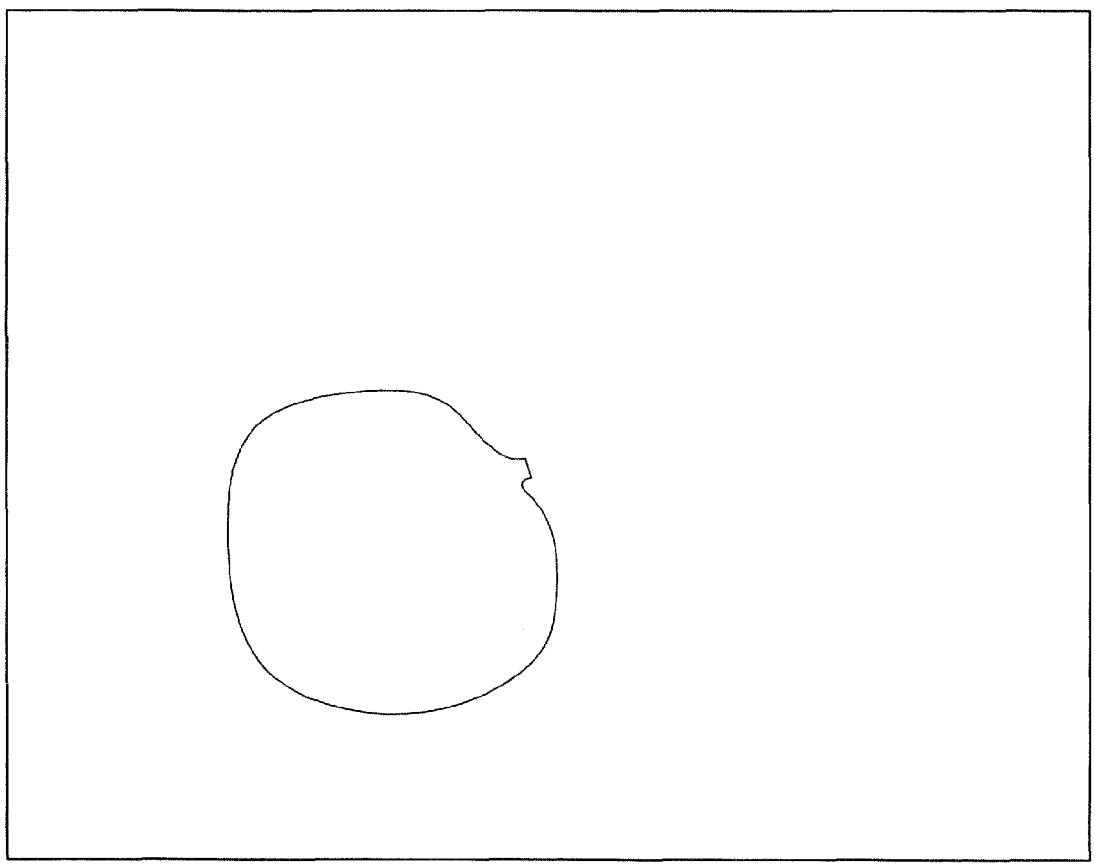
FIG. 5A shows an example of the profile image of the cell body acquired under the first exposure condition.
Figure 5B:
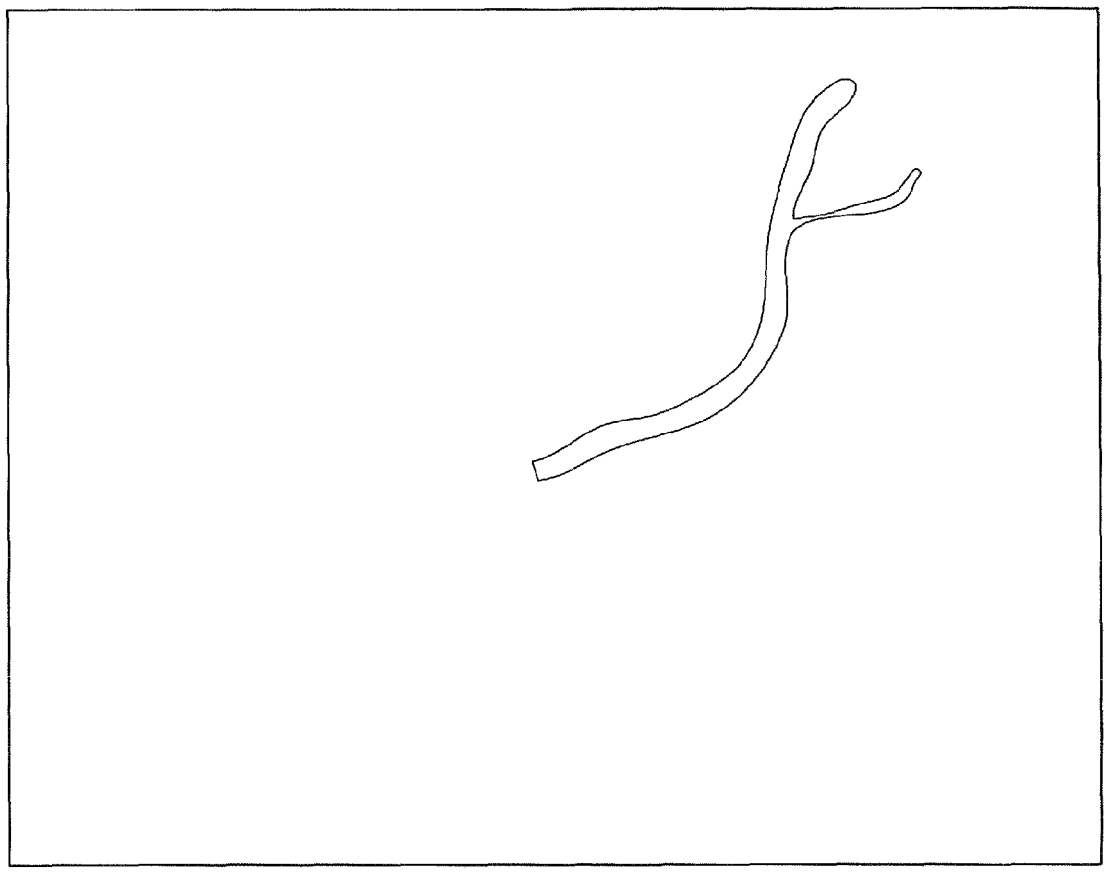
FIG. 5B shows an example of the profile image of the thin projecting part acquired under the second exposure condition.

Next, in the cell image captured under the first exposure condition, the profile in a region covering the cell body of a large area is selected to serve as the first profile image as shown in FIG. 5A (Step S2). In the cell image captured under the second exposure condition, the profile in a region covering the thin projecting part of a slender width is selected to serve as the second profile image as shown in FIG. 5B (Step S3). Step S2 and Step S3 may be in the reverse order.

Figure 6:
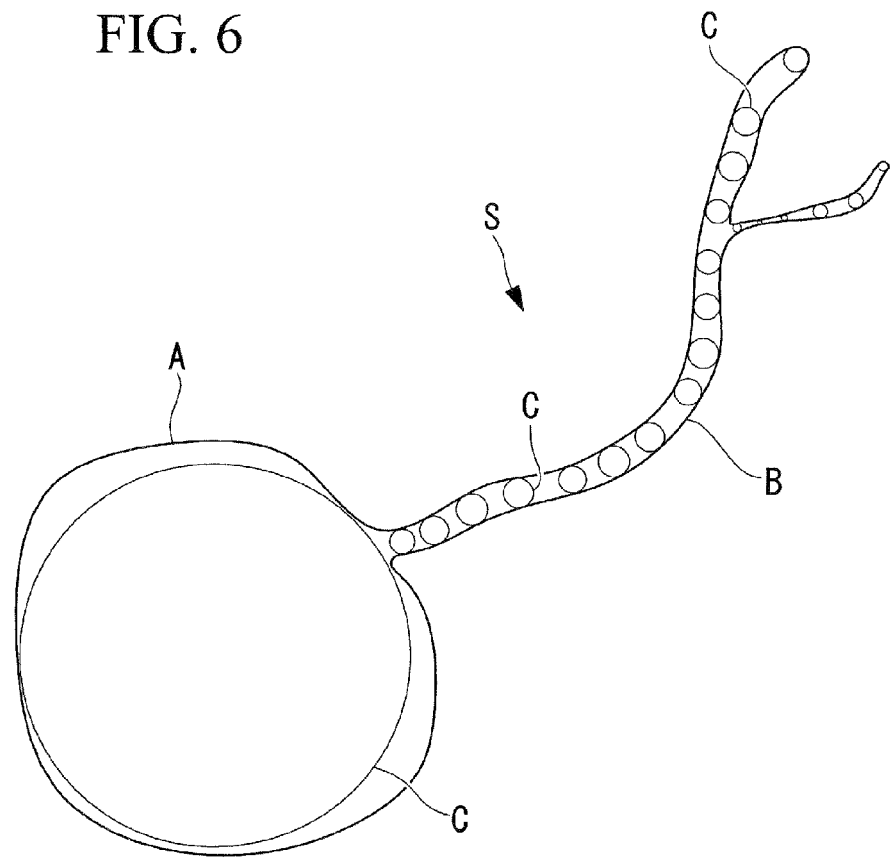
FIG. 6 is an explanatory diagram on a method for selecting the profile shape using the automatic cell analyzer of FIG. 1.

Here, as shown in FIG. 6, the selection between the first and second profile images is performed, for example, of the diameter of an inscribed circle inscribing the profile line. The inscribed circle is drawn in the first or second profile image selected as the above manner.

As shown in FIG. 6, if the diameter of the inscribed circle C is larger than a predetermined value, it is determined that the image is of the cell body A, based on which the profile portion of the cell body A is selected from the first profile image. In addition, if the diameter of the inscribed circle C is smaller than the predetermined value, it is determined that the image is of the thin projecting part B, based on which the profile portion of the thin projecting part B is selected from the second profile image.

In this case, if all cases showing that the radius of the inscribed circle C is smaller than the predetermined value are determined to be the thin projecting part B, discontinuous minute dirt and the like are also regarded as the thin projecting part B. Therefore, such a mistake is prevented by the following manner.

Figure 7:
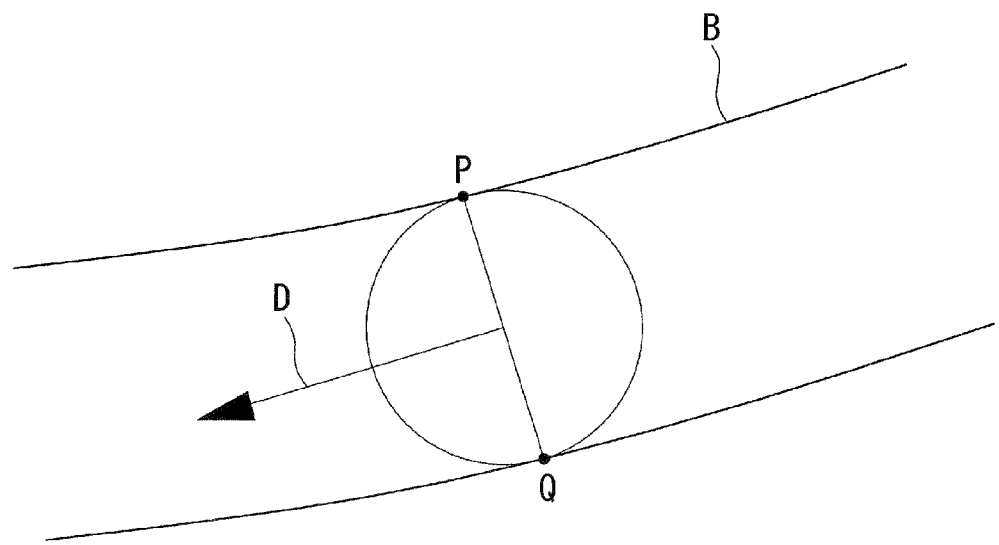
FIG. 7 is an explanatory diagram on a method for selecting the cell in a tubular form using the automatic cell analyzer of FIG. 1.

That is to say, as shown in FIG. 7, in the case of a tubular form such as the thin projecting part B, the inscribed circle C inscribes the profile image at two points which are approximately 180 degrees apart, and there is no profile image in the direction (arrow D) approximately orthogonal to the straight-line linking the inscribed points P and Q. Accordingly, it can be determined that the thin projecting part B is continuous unless the inscribed circle C internally inscribes the profile image in the direction orthogonal to the inscription direction of the circle C, and the thin projecting part B comes to its end when the inscribed circle C internally inscribes another profile image.

As last, the profile portion of the cell body A selected from the first profile image and the profile portion of the thin projecting part B selected from the second profile image are composed (Step S4). By so doing, the profile image showing the whole cell sample S as illustrated in FIG. 6 can be formed.

As described above, with the automatic cell analyzer 1 according to the present embodiment, the profile shape of the cell sample S can be precisely reproduced on the basis of two cell images captured under different exposure conditions. That is to say, an image showing a sharp profile shape without blurring can be achieved for the region of the cell body A having a relatively large area, while an image showing a continuous profile shape without segmentation of the thin projecting part B can be achieved for the region of the thin projecting part. B having a relatively slender form.

As a result, an accurate analysis can be advantageously achieved by precisely figuring out the profile shape of the cell sample S including portions having different dyeing properties, without using a complex dyeing method.

In the present embodiment, the exposure condition is changed by changing the exposure time; however, instead of this, the exposure condition may also be changed by changing the light exposure using the aperture or the like.

In addition, in the present embodiment, two cell images are captured under two exposure conditions for use in the image processing; however, instead of this, three or more cell images may also be captured under three or more exposure conditions.

The invention claimed is:

1. An automatic cell analyzer comprising:
an imaging unit which captures fluorescence emitted from a cell and which acquires a cell image;
an exposure changing section which changes an exposure condition when the imaging unit captures cell images; and
a processing section which analyzes the cell based on a plurality of cell images respectively captured under the changed exposure conditions;
wherein said exposure changing section changes between: (i) a first exposure condition for capturing a first cell image with which a shape of a thin projecting part of the cell can be analyzed, and (ii) a second exposure condition for capturing a second cell image with which a shape of another part of the cell other than the thin projecting part can be analyzed; and
wherein said processing section is configured to detect said thin projecting part based on a diameter of an inscribed circle inscribing a profile shape of each of said cell images.

2. An automatic cell analyzer according to claim 1, wherein said processing section is configured to analyze a nerve cell having the thin projecting part.

3. An automatic cell analyzer according to claim 1, wherein:
said first exposure condition is a condition under which correct exposure can be achieved for the thin projecting part, and
said second exposure condition is a condition under which correct exposure can be achieved for said another part of the cell other than the thin projecting part.

4. An automatic cell analyzing method comprising:
capturing fluorescence emitted from a cell under a first exposure condition, and acquiring a first cell image;
capturing fluorescence emitted from said cell under a second exposure condition that is different from said first exposure condition, and acquiring a second cell image; and
analyzing the cell by detecting a thin projecting part of the cell based on a diameter of an inscribed circle inscribing a profile shape of each of said first cell image and said second cell image.

5. An automatic cell analyzing method according to claim 4, wherein:
said first exposure condition is a condition under which correct exposure can be achieved for a cell body of the cell, and
said second exposure condition is a condition under which correct exposure can be achieved for the thin projecting part extending from the cell body.

6. An automatic cell analyzer according to claim 1, wherein the processing section is configured to determine that the thin projecting part is continuous unless the inscribed circle internally inscribes a profile image in a direction orthogonal to an inscription direction of the circle, and to determine that the thin projecting part comes to an end when the inscribed circle internally inscribes another profile image.

7. An automatic cell analyzing method according to claim 4, wherein analyzing the cell comprises detecting the thin projecting part by determining that the thin projecting part is continuous unless the inscribed circle internally inscribes a profile image in a direction orthogonal to an inscription direction of the circle.

* * * * *